US009204639B2

(12) United States Patent
Mukai et al.

(10) Patent No.: US 9,204,639 B2
(45) Date of Patent: Dec. 8, 2015

(54) PESTICIDE PREPARATION AND PROCESS FOR PRODUCING THE SAME

(71) Applicant: BAYER INTELLECTUAL PROPERTY GMBH, Monheim (DE)

(72) Inventors: Keiichiro Mukai, Oyama (JP); Atsushi Sato, Kawasaki (JP)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 7 days.

(21) Appl. No.: 14/348,243

(22) PCT Filed: Oct. 4, 2012

(86) PCT No.: PCT/EP2012/069556
§ 371 (c)(1),
(2) Date: Mar. 28, 2014

(87) PCT Pub. No.: WO2013/050433
PCT Pub. Date: Apr. 11, 2013

(65) Prior Publication Data
US 2014/0228220 A1 Aug. 14, 2014

(30) Foreign Application Priority Data
Oct. 5, 2011 (JP) .................................. 2011-221411

(51) Int. Cl.
*A01N 43/08* (2006.01)
*A01N 25/10* (2006.01)
*A01N 25/12* (2006.01)

(52) U.S. Cl.
CPC ....................................... *A01N 43/08* (2013.01)

(58) Field of Classification Search
CPC ........ A01N 25/10; A01N 25/12; A01N 43/08
See application file for complete search history.

(56) References Cited

U.S. PATENT DOCUMENTS

2004/0259736 A1* 12/2004 Dieing ................... A01N 25/10
504/360

FOREIGN PATENT DOCUMENTS

| EP | 0529975 A1 | 3/1993 | |
|---|---|---|---|
| EP | 0529975 A1 * | 3/1993 | ............. A01N 47/36 |
| JP | S 6335504 A | 2/1988 | |
| JP | S 6345201 A | 2/1988 | |
| JP | H 02288803 A | 11/1990 | |
| JP | 2003-171207 A | 6/2003 | |
| JP | 2003171207 A * | 6/2003 | ............. A01N 25/12 |
| WO | 03028453 A1 | 4/2003 | |
| WO | 2005029956 A1 | 4/2005 | |

OTHER PUBLICATIONS

XP-002691252 "Manufacture of agrochemical granule for use in agriculture, by mix-heating active ingredients, thermoplastic material and carrier, cooling, and granulating under predefined conditions", (2003) Thomson; pp. 1-2.
Weed Research 26 (1986) 441-445 (Cited on p. 4 of the Specification).
The Pesticide Manual, the 15th edition, The British Crop 25 Protection Council and the Royal Soc. of Chemistry, 2006 (Cited on page 4 of the Specification).

* cited by examiner

*Primary Examiner* — Jane C Oswecki
(74) *Attorney, Agent, or Firm* — Miles & Stockbridge P.C.

(57) ABSTRACT

A novel pesticide preparation, which can be easily produced at a low cost and has sustained release properties, is provided. A pesticide preparation containing a pesticide active ingredient and a heat-meltable material and/or a thermoplastic material, the pesticide preparation further containing an amine being capable of forming an associated state with the pesticide active ingredient and containing a group having a hydrophobic moiety on a nitrogen atom.

17 Claims, No Drawings

PESTICIDE PREPARATION AND PROCESS FOR PRODUCING THE SAME

CROSS REFERENCE TO RELATED APPLICATIONS

This application is a §371 National Stage Application of PCT/EP2012/069556, filed Oct. 4, 2012 which claims priority to JP 2011-221411, filed Oct. 5, 2011.

BACKGROUND

1. Field of the Invention

The present invention relates to a pesticide preparation (pesticide composition) and a process for producing the same.

2. Description of Related Art

The release control of a pesticide can be commonly achieved by microencapsulating a drug, coating a drug with a polymer material, or dispersing a drug in a water-insoluble preparation matrix (Non-Patent Literature 1).

For example, the methods for achieving sustained release by adding paraffin wax, a thermoplastic resin or activated carbon, a granular foam or a clay mineral in combination have been proposed (see Patent Literatures 1 to 3).

Further, Patent Literature 4 proposes a method for achieving sustained release by kneading a thermoplastic material and an inorganic diluent carrier under heating, cooling the obtained kneaded product and extruding it for granulation. The technique described in Patent Literature 4 adjusts the dissolution rate by kneading a hydrophobic wax and a hydrophilic wax. However, it requires the precise temperature control near the melting point to prevent the kneaded product from liquefying or separating into two layers. Furthermore, the cost for raw materials is presumably high since a large amount of waxes is contained.

Moreover, Patent Literature 5 proposes a method for achieving sustained release of an active ingredient, by using a cationic surfactant (amine salt-, pyridinium-, or quaternary ammonium salt-based surfactant, or the like) and an inorganic basic substance (calcium carbonate, or the like), for the purpose of controlling dissolution of a granular pesticide preparation containing a pesticide active ingredient. Examples of the amine cationic surfactant include long chain alkylamine salts (laurylamine chloride, stearylamine chloride, and the like).

PRIOR ART LITERATURE

Patent Literature

[Patent Literature 1] Japanese Patent Application Publication No. 63-35504
[Patent Literature 2] Japanese Patent Application Publication No. 63-45201
[Patent Literature 3] Japanese Patent Application Publication No. 02-288803
[Patent Literature 4] Japanese Patent Application Publication No. 2003-171207
[Patent Literature 5] International Publication No. WO2005/029956

Non-Patent Literature

[Non Patent Literature 1] "Noyaku seizai gaido (in Japanese) ("Pesticide Preparations Handbook")" (1997), edited by Pesticide Science Society of Japan, Noyaku seizai Shiyoho Kenkyukai (in Japanese) (Pesticide Preparations and Applications Workshop), published by JAPAN PLANT PROTECTION ASSOCIATION

SUMMARY

The conventional techniques for controlling dissolution of a pesticide required precise temperature control, enormous raw material cost and production cost.

Thus, an object of the present invention is to provide a novel pesticide preparation which improves the above problems, can be easily produced at a low cost and has sustained release properties.

The present inventors have conducted extensive studies to solve the problems described above and found that good sustained release properties can be achieved by adding an amine being capable of forming an association with the pesticide active ingredient and a heat-meltable material and/or a thermoplastic material to a pesticide preparation, and accomplished the present invention.

More specifically, the first aspect of the present invention relates to a pesticide preparation containing a pesticide active ingredient and a heat-meltable material and/or a thermoplastic material, the pesticide preparation further containing an amine being capable of forming an associated state with the pesticide active ingredient and containing a group having a hydrophobic moiety on a nitrogen atom.

The second aspect of the present invention relates to the above-mentioned pesticide preparation wherein the amine is represented by the following general formula (I)

wherein $R^1$ is a group having 3 to 20 carbon atoms as the group having a hydrophobic moiety, $R^2$ and $R^3$ are independently a hydrogen atom or a saturated or unsaturated, substituted or unsubstituted hydrocarbon group.

The third aspect of the present invention relates to the above-mentioned pesticide preparation, wherein the hydrophobic moiety of the amine is an aromatic ring.

The forth aspect of the present invention relates to the above-mentioned pesticide preparation, wherein the hydrophobic moiety of the amine is a substituted or unsubstituted phenyl group or phenylene group.

The fifth aspect of the present invention relates to the above-mentioned pesticide preparation, wherein the group having the hydrophobic moiety of the amine is a group selected from the group consisting of a substituted or unsubstituted phenyl group, benzyl group, pyridyl group, pyrrolyl group, quinolyl group, toluidyl group, indolyl group, imidazolyl group and pyrazyl group.

The sixth aspect of the present invention relates to the above-mentioned pesticide preparation, wherein the amine is at least one amine selected from the group consisting of aniline, diphenylamine, N,N-dimethylaniline, N-methylaniline, N,N-diethylaniline, N-ethylaniline and dibenzylamine.

The seventh aspect of the present invention relates to the above-mentioned pesticide preparation, wherein the amine is at least one amine selected from the group consisting of diphenylamine, N,N-dimethylaniline and N-methylaniline.

The eighth aspect of the present invention relates to the above-mentioned pesticide preparation, wherein the pesticide active ingredient comprises a herbicide for paddy field weeds.

The ninth aspect of the present invention relates to the above-mentioned pesticide preparation, wherein the pesticide active ingredient comprises at least one compound selected from the group consisting of pyrimisulfan, triafamone, tefuryltrione, ketospiradox, mesotrione, sulcotrione and tembotrione.

The tenth aspect of the present invention relates to the above-mentioned pesticide preparation, wherein the heat-meltable material and/or thermoplastic material is a wax, polycyclic aromatic hydrocarbon or a mixture thereof.

The eleventh aspect of the present invention relates to the above-mentioned pesticide preparation, further comprising a carrier, the carrier being an oil absorbent carrier selected from the group consisting of calcium montmorillonite, attapulgite, pumice, perlite, diatomaceous earth, vermiculite, talc and clay.

The twelfth aspect of the present invention relates to a process for producing the above-mentioned pesticide preparation, the process comprising a step of mixing a pesticide active ingredient, an amine being capable of forming an associated state with the pesticide active ingredient and containing a group having a hydrophobic moiety on a nitrogen atom, a heat-meltable material and/or a thermoplastic material, and a carrier under heating.

The present invention further relates to the use of an amine, being capable of forming an associated state with a pesticide active ingredient and containing a group having a hydrophobic moiety on a nitrogen atom, in the production of a pesticide preparation. Furthermore, the present invention relates to the use of the amine represented by the above general formula (I) in the production of a pesticide preparation.

The present invention still further relates to the pesticidal use of a preparation containing a pesticide active ingredient and an amine being capable of forming an associated state with the pesticide active ingredient and containing a group having a hydrophobic moiety on a nitrogen atom.

DETAILED DESCRIPTION OF A PREFERRED EMBODIMENT

The pesticide preparation of the present invention has good sustained release properties by containing the amine being capable of forming an association with a pesticide active ingredient and containing a group having a hydrophobic moiety on a nitrogen atom.

Hereinbelow, the present invention is described in detail in reference to the embodiments. All literatures referred to in this specification are considered incorporated as a whole into the content of the specification of this application.

The pesticide preparation of the present invention is characterized in that the pesticide preparation contains a pesticide active ingredient, amine and a heat-meltable material and/or a thermoplastic material, and the amine is an amine is capable of forming an associated state with the pesticide active ingredient and contains a group having a hydrophobic moiety on a nitrogen atom.

The pesticide active ingredient contained in the pesticide preparation of the present invention is not particularly limited insofar as it forms an association with the amine containing a group having a hydrophobic moiety on a nitrogen atom. Usual ones are herbicides, plant growth regulators, fungicides, insecticides, etc., including the geometrical isomer, optical isomer, etc., thereof. Preferable ingredients are those acidic or polar, or those having an aromatic ring. Further, pesticide active ingredients for paddy fields are desirable.

Examples of the herbicide and plant growth regulator are known active substances acting as the inhibitor of acetolactic acid synthase, acetyl-CoA carboxylase, cellulose synthase, enolpyruvylshikimic acid-3-phosphoric acid synthase, glutamine synthase, p-hydroxyphenylpyruvic acid dioxygenase, phytoene desaturase, photo system I, photo system II, and protoporphyrinogen oxidase, and described in, e.g., Weed Research 26 (1986) 441-445 or "The Pesticide Manual", the 15th edition, The British Crop Protection Council and the Royal Soc. of Chemistry, 2006 and the literature cited therein.

More specifically, examples include the following active substances (chemical compounds are referred to either by the "common name" in accordance with the International Organization for Standardization (ISO) or by their chemical name or code number). Further, the examples always encompass all application forms such as acids, salts and esters, and isomers including variations such as stereoisomer and optical isomer. Examples of at least one application form and/or variation are given below:

acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminocyclopyrachlor-methyl, aminocyclopyrachlor-potassium, aminopyralid, amitrole, ammonium sulfamate, ancymidol, anilofos, asulam, atrazine, azafenidin, azimsulfuron, aziprotryn, beflubutamid, benazolin, benazolin-ethyl, bencarbazone, benfluralin, benfuresate, bensulide, bensulfuron, bensulfuron-methyl, bentazon, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidone, cinidon-ethyl, cinmethylin, cinosulfuron, clethodim, clodinafop, clodinafop-propalgyl, clofencet, clomazone, clomeprop, cloprop, clopyralid, cloransulam, chloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamide, dimethenamide-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanide, F-5331, i.e., N-[2-chloro-4-fluoro-5-[4-(3-fluoropropyl)-4,5-dihydro-5-oxo-1H-tetrazol-1-yl]phenyl]-ethanesulfonamide, F-7967, i.e., 3-[7-chloro-5-fluoro-2-(trifluoromethyl)-1H-benzimidazol-4-yl]-1-methyl-6-

(trifluoromethyl)pyrimidine-2,4-(1H,3H)-dione, fenoprop, fenoxaprop, fenoxaprop-P, fenoxaprop-ethyl, fenoxaprop-P-ethyl, fenoxasulfone, fentrazamide, fenulon, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbozone-sodium, flucetosulfuron, fluchloralin, flufenacet (thiafluamide), flufenpyr, flufenphyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e., O-(2,4-dimethyl-6-nitrophenyl)-O-ethyl-isopropylphosphoramidethioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyhop-P-methyl, hexadinone, HW-02, i.e., 1-(dimethoxyphosphoryl)-ethyl-(2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indol-3-yl acetate (IAA), 4-indol-3-yl-butyric acid (IBA), iodosulfuron, iodosulfuron-methyl-sodium, iofensulfuron, iofensulfuron-sodium, ioxynil, ipfencarbazone, isocarbamide, isopropaline, isoproturon, isouron, isoxaben, isoxachlortole, isoxaflutole, isoxapyrifop, KUH-043, i.e., 3-({[5-(difluoromethyl)-1-methyl-3-(trifluoromethyl)-1H-pyrazol-4-yl]methyl}sulfonyl)-5,5-dimethyl-4,5-dihydro-1,2-oxazol, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldimuron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogen sulfate, monolinuron, monosulfuron, monosulfuron-ester, monuron, MT 128, i.e., 6-chloro-N-[(2E)-3-chloroprop-2-en-1-yl]-5-methyl-N-phenylpyridazine-3-amine, MT-5950, i.e., N-[3-chloro-4-(1-methylethyl)-phenyl]-2-methylpentanamide, NGGC-011, naproanilide, napropamide, naptalam, NC-310, i.e., 4-(2,4-dichlorobenzoyl)-1-methyl-5-benzyloxypyrazole, neburon, nicosulfuron, nipyraclofen, nitralin, nitrofen, nitrophenolato-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat-dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pyriphenop, pyriphenop-butyl, pretilachlor, primisulfuron, primisulfuron-methyl, probenazole, profluazol, procyazin, prodiamine, profluraline, profoxydim, prohexadione, prohexadione-calcium, prohydrojasmon, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e., methyl-(2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SW-065, SYN-523, SYP-249, i.e., 1-ethoxy-3-methyl-1-oxobut -3-en-2-yl-5-[2-chloro-4-(trifluoromethyl)phenoxy]-2-nitrobenzoate, SYP-300, i.e., 1-[7-fluoro-3-oxo-4-(prop-2-yn-1-yl)-3,4-dihydro-2H-1,4-benzoxadin-6-yl]-3-propyl-2-thioxoimidazolidin-4,5-dione, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e., 3,4-dichloro-{2-[4,6-dimethoxypyrimidin-2-yl)oxy]benzyl}aniline, and the following compounds:

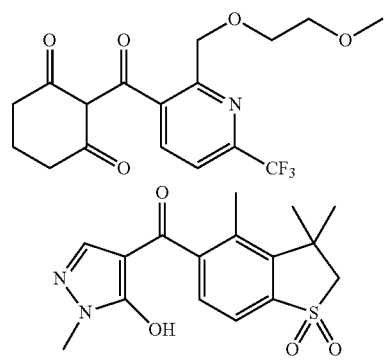

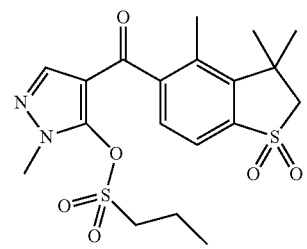

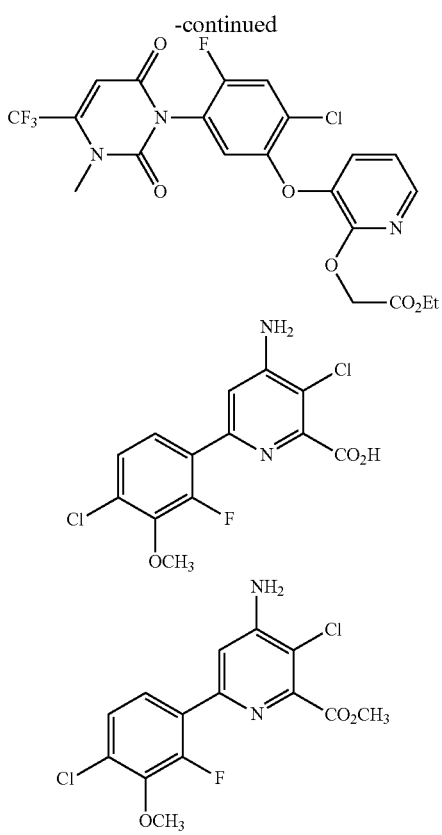

Hereinafter, examples of the herbicides usable in the present invention are given categorized under each mechanism of action.

Acetyl-CoA Carboxylase (ACCase) Inhibitors
  Aryloxyphenoxypropionic acid ACCase inhibitors: clodinafop-propalgyl, cyhalofop-butyl, diclofop-methyl, fenoxaprop-P-ethyl, fluazifop-P-butyl, haloxyfop-R-methyl, propaquizafop, quizalofop-P-ethyl, metamifop
  Cyclohexanedione ACCase inhibitors: alloxydim, butroxydim, clethodim, cycloxydim, profoxydim, sethoxydim, tepraloxydim, tralkoxydim
  Phenylpyrazoline ACCase inhibitor: pinoxaden
Acetolactate Synthase (ALS) inhibitors
  Sulfonyl urea ALS inhibitors: amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-Na, foramsulfuron, halosulfuron-methyl, imazosulfuron, iodosulfuron, mesosulfuron-methyl, metsulfuron-methyl, nicosulfuron, oxasulfuron, primisulfuron-methyl, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron, orthosulfamron, TH547, NC620
  Imidazolinone (ALS) inhibitors: imazapic, imazamethabenz-methyl, imazamox, imazapyr, imazaquin, imazethapyr
  Triazolopyrimidine ALS inhibitors: cloransulam-methyl, diclosulam, florasulam, flumetsulam, metosulam, penoxsulam
  Pyrimidinylsalicylic acid ALS inhibitors: bispyribac-sodium salt, pyribenzoxim, pyriftalid, pyrithiobac-sodium salt, pyriminobac-methyl, pyrimisulfan
  Triazolinone ALS inhibitors: flucarbazone-sodium salt, propoxycarbazone-sodium salt, thiencarbazone
Photosynthesis Inhibitors (Photosystem II)
  Triazine type: ametryn, atrazine, cyanazine, desmetryn, dimethametryn, prometon, prometryn, propazine, simazine, simetryn, terbumeton, terbuthylazine, terbutryn, trietazine
  Triazinone type: hexadinone, metamitron, metribuzin
  Triazolinone type: amicarbazone
  Uracil type: bromacil, lenacil, terbacil
  Pyridazinone type: Chloridazon
  Phenylcarbamate type: desmedipham, phenmedipham
  Urea type: chlorbromuron, chlorotoluron, chloroxuron, dimefuron, diuron, ethidimuron, fenuron, fluometuron, isoproturon, isouron, linuron, methabenzthiazuron, metobromuron, metoxuron, monolinuron, neburon, siduron, tebuthiuron
  Amide type: propanil, pentanochlor
  Nitrile type: bromofenoxim, broxynil, ioxynil
  Benzothiadiazinone type: bentazon
  Phenyl pyridazine type: pyridate, pyridafol
Toxicity Expression Agents by Photoactivation (Photosystem II)
  Bipyridinium type: diquat, paraquat
Protoporphyrinogen Oxitase (PPO) Inhibitors
  Diphenyl-ether type: acifluorfen, bifenox, chlomethoxyfen, fluoroglycofen, fomesafen, halosafen, lactofen, oxyfluorfen, chlomethoxynil
  Phenylpyrazole type: fluazolate, pyraflufen-ethyl
  N-phenylphthalimide type: cinidon-ethyl, flumioxazin, flumiclorac-pentyl
  Thiadiazole type: fluthiacet-methyl, thidiazimin
  Oxadiazole type: oxadiazon, oxadiargyl
  Triazolinone type: azafenidin, carfentrazone-ethyl, sulfentrazone
  Oxazolidinedione type: pentoxazone
  Pyrimidinedione type: benzfendizone, butafenacil
  Others: pyraclonil, profluazol, flufenpyr-ethyl
Carotinoide Biosynthesis Inhibitors
  1. PDS inhibitors
  Pyridazinone type: norflurazon
  Pyridinecarboxyamide type: diflufenican, picolinafen
  Others: beflubutamid, fluridone, fluorochloridone, flurtamone
  2. 4-HPPD inhibitors
  Triketone type: mesotrione, sulcotrione, benzobicyclon, tefuryltrione
  Isoxazole type: isoxachlortole, isoxaflutole
  Pyrazole type: benzofenap, pyrazolynate, pyrazoxyfen
  Others: benzobicyclon
  3. Inhibitors with unknown target
  Triazole type: amitrole
  Isoxazolidinone type: clomazone
  Diphenylether type: aclonifen
EPSP Synthetase Inhibitors
  Glycine type: glyphosate, glyphosate-trimesium salt
Glutamine Synthetase Inhibitors
  Phosphinic-acid type: glufosinate, bialaphos
DHP biosynthesis inhibitors
  Carbamate type: asulam
Microtubule Polymerization Inhibitors
  Dinitroaniline type: bethrodine, butralin, dinitramine, ethalfluralin, oryzalin, pendimethalin, trifluralin
  Phosphoric amide type: amiprophos methyl, butamifos
  Pyridine type: dithiopyr, thiazopyr
  Benzamide type: propyzamide, tebutam, chlorthal-dimethyl Mitosis/Microtuble Formation Inhibitors
  Carbamate type: chlorpropham, propham, carbetamide
Very-Long-Chain Fatty Acid Biosynthesis Inhibitors
  Chloroacetamide type: acetochlor, alachlor, butachlor, dimethachlor, dimethenamide, metazachlor, metolachlor, pethoxamid, pretilachlor, propachlor, propisochlor, thenylchlor
  Acetamide type: diphenamid, napropamide, naproanilide
  Oxyacetamide type: flufenacet, mefenacet
  Tetrazolinone type: fentrazamide
  Others: anilofos, cafenstrole, piperophos
Cellulose Biosynthesis Inhibitors
  Nitrile type: dichlobenil, chlorthiamid
  Benzamide type: isoxaben
  Triazolo carboxamide type: flupoxam
  Quinolinecarboxylic acid type: quinclorac
Uncouplers
  Dinitrophenol type: DNOC, dinoseb, dinoterb
Fatty Acid Extension Inhibitors (Non-ACCase Inhibition)
  Thiocarbamates: butylate, cycloate, dimepiperate, EPTC, esprocarb, molinate, orbencarb, pebulate, prosulfocarb, benthiocarb, pyributicarb, tiocarbazil, tri-allate, vernolate
  Dithiophosphorate type: bensulide
  Benzofuran type: benfuresate, ethofumesate
  Chlorocarbonick acid type: TCA, dalapon, tetrapion
Auxin-Type Herbicides
  Phenoxycarboxylic acid type: clomeprop, 2,4-D, 2,4-DB, dichlorprop, MCPA, MCPB, MCPP
  Benzoic acid type: chloramben, dicamba, 2,3,6-TBA
  Pyridinecarboxlic-acid type: clopyralid, fluoroxypyr, picloram, triclopyr, quinclorac, quinmerac
  Others: benazolin-ethyl
Auxin Transport Inhibitors
  Naptalamate type: naptalam
  Semicarbazone type: diflufenzopyr-sodium salt
Others (Action Mechanism Unknown)
  Aryl aminopropionic acid type: flamprop-M-methyl, flamprop-isopropyl
  Pyrazolium type: difenzoquat
  Organic arsenic type: DSMA, MSMA
  Others: bromobutide, chlorflurenol, cinmethylin, cumyluron, dazomet, dymron, methyldymuron, etobenzanide, fosamine, indanofan, metam, oxaziclomefone, oleic acid, pelargonic acid, pyributicarb Preferable herbicides include those comprising sulfonyl urea compounds, sulfone anilide compounds, benzoyl cyclohexanedione compounds or salts thereof. Particularly preferable examples include pyrimisulfan, triafamone, and the like given as sulfone anilide compounds. Moreover, examples of benzoyl cyclohexanedione compounds include tefuryltrione, ketospiradox, mesotrione, sulcotrione, and tembotrione.

The pesticide active ingredient contained in the sustained release pesticide preparation of the present invention is not particularly limited, and examples of the fungicide include the following:

(1) Ergosterol biosynthesis inhibitors, e.g., aldimorph, azaconazole, bitertanol, bromuconazole, cyproconazole, diclobutrazol, difenoconazole, diniconazole, diniconazole-M, dodemorph, dodemorph-acetate, epoxyconazole, ethaconazole, fenarimol, fenbuconazole, fenhexamid, fenpropidine, fenpropimorph, fluquinconazole, flurprimidol, flusilazole, flutriafol, fluconazole, fluconazole-cis, hexaconazole, imazalil, imazalilsulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimideformamide, N-ethyl-N-methyl-N'-{2-methyl-5-(trifluoromethyl)-4-[3-(trimethylsilyl)propoxy]phenyl}imideformamide, O-[1-(4-methoxyphenoxy)-3,3-dimethylbutan-2-yl]1H-imidazole-1-carbothioate (2) Complex I or II respiratory chain inhibitors, e.g., bixafen, boscalid, carboxin, diflumetorim, fenfuram, fluopyram, flutolanil, fluxapyroxad, furametpyr, furmecyclox, isopyrazam (mixtures of syn-epimeric racemate 1RS, 4SR, 9RS and anti-epimeric racemate 1RS, 4SR, 9SR), isopyrazam (anti-epimeric racemate 1RS, 4SR, 9SR), isopyrazam (anti-epimeric enantiomer 1R,4S,9S), isopyrazam (anti-epimeric enantiomer 1S,4R,9R), isopyrazam (syn-epimeric racemate 1RS, 4SR, 9RS), isopyrazam (syn-epimeric enantiomer 1R,4S,9R), isopyrazam (syn-epimeric enantiomer 1S, 4R,9S), mepronil, oxycarboxin, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazolin-4-amine, N-[9-(dichloromethylene)-1,2,3,4-tetrahydro-1,4-methanonaphthalen-5-yl]-3-(difluoromethyl)-1-methyl -1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide (3) Complex III respiratory chain inhibitors, e.g., ametocradin, amisulbrom, azoxystrobin, cyazofamid, cou-methoxystrobin, cou-moxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N -methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl(2E)-2-{2-[({cyclopropyl[(4-methoxyphenyl)
imino]methyl}sulfanyl)methyl]phenyl}-3-methoxyprop-
2-enoate, N-(3-ethyl-3,5,5-trimethylcyclohexyl)-3-
(formylamino)-2-hydroxybenzamide, 2-{2-[(2,5-
dimethylphenoxy)methyl]phenyl}-2-methoxy-N-
methylacetamide, (2R)-2-{2-[(2,5-dimethylphenoxy)
methyl]phenyl}-2-methoxy-N-methylacetamide (4) Mitosis and cell division inhibitors, e.g., benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl) [1,2,4]triazolo[1,5-a]pyrimidine, 3-chloro-5-(6-chloropyridin-3-yl)-6-methyl-4-(2,4,6-trifluorophenyl)pyridazine (5) Compounds capable of having multi-moiety actions, e.g., Bordeaux mixture, captafol, captan, chlorothalonil, copper hydroxide, copper naphthenate, copper oxide, copper oxychloride, copper sulfate, dichlofluanid, dithianon, dodine, dodine free base, ferbam, fluorfolpet, folpet, guazatine, guazatine acetate, iminoctadine, iminoctadine albesilate, iminoctadine triacetate, mancupper, mancozeb, maneb, metiram, metiram-zinc, oxine-copper, propamidine, propineb, sulfur and sulfur preparations containing calcium polysulfide, thiram, tolyfluanid, zineb, ziram (6) Compounds capable of inducing host defense, e.g., acibenzolar-S-methyl, isotianil, probenazole, tiadinil (7) Amino acid and/or protein biosynthesis inhibitors, e.g., andoprim, blasticidin-S, cyprodinil, kasugamycin, kasugamycin hydrochloride hydrate, mepanipyrim, pyrimethanil, 3-(5-fluoro-3,3,4,4-tetramethyl-3,4-dihydroisoquinolin-1-yl)quinoline (8) ATP production inhibitors, e.g., fentin acetate, fentin chloride, fentin hydroxide, silthiofam (9) Cell wall synthesis inhibitors, e.g., benthiavalicarb, dimethomorph, flumorph, iprovalicarb, mandipropamid, polyoxin, polyoxorim, validamycin A, valifenalate

(10) Lipid and membrane synthesis inhibitors, e.g., biphenyl, chloroneb, dicloran, edifenphos, etridiazol, iodocarb, iprobenfos, isoprothiolane, propamocarb, propamocarb hydrochloride, prothiocarb, pyrazophos, quintozene, tecnazene, tolclophos-methyl

(11) Melanin biosynthesis inhibitors, e.g., calpropamide, diclocymet, fenoxanil, phthalide, pyroquilone, tricyclazole, 2,2,2-trifluoroethyl{3-methyl-1-[(4-methylbenzoyl)amino]butan-2-yl}carbamate

(12) Nucleic acid synthesis inhibitors, e.g., benalaxyl, benalaxyl-M (chiralaxyl), bupirimate, clozylacon, dimethirimol, ethirimol, furalaxyl, hymexazol, metalaxyl, metalaxyl-M (mefenoxam), ofurace, oxadixyl, oxolinic acid

(13) Signal transduction inhibitors, e.g., chlozolinate, fenpiclonil, fludioxonil, iprodione, procymidone, quinoxyfen, vincrozolin

(14) Compounds capable of serving as uncoupler, e.g., binapacryl, dinocap, ferimzone, fluazinam, meptyldinocap

(15) Other compounds, e.g., benthiazole, bethoxazin, capcimycin, carvone, quinomethionate, pyriofenone (chlazafenone), cufraneb, cyflufenamid, cymoxanil, ciprosulfamide, dazomet, devacarb, dichlorophen, diclomezine, difenzoquat, difenzoquat methylsulfate, diphenylamine, ecomate, fenpyrazamine, flumetover, fluoroimide, flusulfamide, flutianil, fosetyl-aluminum, fosetyl-calcium, fesetyl-sodium, hexachlorobenzene, irumamycin, methasulfocarb, methylisothiocyanate, metrafenone, mildiomycin, natamycin, nickel dimethyldithiocarbamate, nitrotal isopropyl, octhilinone, oxamocarb, oxyfenthiin, pentachlorophenol and salts thereof, phenothrin, phosphorous acid and salts thereof, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrroInitrin, tebufloquin, techlofthalam, tolnifanide, triazoxide, trichlamide, zarilamid, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonon-7-yl-2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol -1-yl]ethanone, 1-(4-{4-[5-(2,6-difluorophenyl)-4,5-dihydro-1,2-oxazol-3-yl]-1,3-thiazol-2-yl}piperidin -1-yl)-2-[5-methyl-3-(trifluoromethyl)-1H-pyrazol-1-yl]ethanone, 1-(4-methoxyphenoxy)-3,3-dimethylbutan-2-yl-1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2,6-dimethyl-1H,5H-[1,4]-dithiino[2,3-c:5,6-c']dipyrrole-1,3,5,7(2H,6H)-tetron, 2-[5-methyl-3-(trifluoromethyl)-1H-pyrazol-1-yl]-1-(4-{4-[(5R)-5-phenyl-4,5-dihydro-1,2-oxazol-3-yl]-1,3-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[5-phenyl-4,5-dihydro-1,2-oxazol-3-yl]-1,3-thiazol-2-yl}piperidin-1-yl)ethanone, 2-butoxy-6-iodo-3-propyl-4H -chromen-4-one, 2-chloro-5-[2-chloro-1-(2,6-difluoro-4-methoxyphenyl)-4-methyl-1H-imidazol-5-yl]pyridine, 2-phenylphenol and salts thereof, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophenon-2-sulfonohydrazide, 5-fluoro-2-[(4-fluorobenzyl)oxy]pyrimidine-4-amine, 5-fluoro-2-[(4-methylbenzyl)oxy]pyrimidine-4-amine, 5-methyl-6-octyl[1,2,4]triazolo[1,5-a]pyrimidine-7-amine, ethyl(2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimideformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-(E)-[(cyclopropylmethoxy)imino][6-(difluoromethoxy)-2,3-difluorophenyl]methyl-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimideformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl -2-(1-{[5-methyl-3-(trifluoromethyl)-1H-pyrazol-1-yl]acetyl}piperidin-4-yl)-N-[(1R)-1,2,3,4- tetrahydronaphthalen-1-yl]-1,3-thiazole-4-carboxamide, N-methyl-2-(1-{[5-methyl-3-(trifluoromethyl) -1H-pyrazol-1-yl]acetyl}piperidin-4-yl)-N-[(1S)-1,2,3,4-tetrahydronaphthalen-1-yl]-1,3-thiazole-4-carboxamide, pentyl{6-[({[(1-methyl-1H-tetrazol-5-yl)(phenyl) methylidene]amino}oxy)methyl]pyridin -2-yl}carbamate, phenazine-1-carboxylic acid, quinolin-8-ol, quinolin-8-ol-sulfate (2:1), tert-butyl{6-[({[(1-methyl-1H-tetrazol-5-yl)(phenyl)methylene]amino}oxy)methyl]pyridin-2-yl}carbamate

(16) Still other compounds, e.g., 1-methyl-3-(trifluoromethyl)-N-[2'-(trifluoromethyl)biphenyl-2-yl]-1H -pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N -(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro -1,3-dimethyl-N-[4'-(prop-1-yn-1-yl)biphenyl-2-yl]-1H-pyrazole-4-carboxamide, 2-chloro-N-[4'-(prop-1-yn-1-yl) biphenyl-2-yl]pyridine-3-carboxamide, 3-(difluoromethyl)-N-[4'-3,3-dimethylbut-1-yn-1-yl) -biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)-biphenyl-2-yl]-1-methyl-1H-pyrazole-4-carboxamide, 5-fluoro-N-[4'-(3-methoxy -3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl) ethyl]-N2-(methylsulfonyl)valinamide, 4-oxo-4-[(2-phenylethyl)amino]butanoic acid, but-3-yn-1-yl {6-[({ [(Z)-(1-methyl-1H-tetrazol-5-yl)(phenyl) methylene] amino}oxy)methyl]pyridin-2-yl}carbamate The compounds categorized into the above (1) to (16) may form a salt with a suitable base or acid as long as a functional group accepts.

Examples of the insecticide as the pesticide active ingredient of the present invention include the following. The active ingredients specified by the "common name" are known or described in, for example, Pesticide Manual ("The Pesticide Manual", 14th Ed., British Crop Protection Council 2006) or can be searched on the Internet (e.g., http://www.alanwood.net/pesticides).

(1) Acetylcholinesterase (AChE) inhibitors, e.g., carbamate type such as alanycarb (II-1-1), aldicarb (II-1-2), bendiocarb (II-1-3), benfuracarb (II-1-4), butoxycarboxim (II-1-5), butoxycarboxim (II-1-6), carbaryl (II-1-7), carbofuran (II-1-8), carbosulfane (II-1-9), ethiofencarb (II-1-10), fenobucarb (II-1-11), formetanate (II-1-12), furathiocarb (II-1-13), isoprocarb (II-1-14), methiocarb (II-1-15), methomyl (II-1-16), metolcarb (II-1-17), oxamyl (II-1-18), pirimicarb (II-1-19), propoxur (II-1-20), thiodicarb (II-1-21), thiofanox (II-1-22), triazamate (II-1-23), trimetacarb (II-1-24), XMC (II-1-25), xylylcarb (II-1-26); and organophosphate type, such as acephate (II-1-27), azamethiphos (II-1-28), azinphos-ethyl (II-1-29), azinphosmethyl (II-1-30), cadusafos (II-1-31), chlorethoxyfos (II-1-32), chlorfenvinphos (II-1-33), chlormephos (II-1-34), chlorpyrifos (II-1-35), chlorpyrifos-methyl (II-1-36), coumaphos (II-1-37), cyanophos (II-1-38), demeton-S-methyl (II-1-39), diazinon (II-1-40), dichlorvos/DDVP (II-1-41), dicrotophos (II-1-42), dimethoate (II-1-43), dimethylvinphos (II-1-44), disulfoton (II-1-45), EPN (II-1-46), ethion (II-1-47), ethoprophos (II-1-48), famphur (II-1-49), fenamiphos (II-1-50), fenitrothion (II-1-51), fenthion (II-1-52), fosthiazate (II-1-53), heptenophos (II-1-54), imicyafos (II-1-55), isofenphos (II -1-56), isopropyl O-(methoxyaminothio-phosphoryl)salicylate (II-1-57), isooxathione (II-1-58), malathion (II-1-59), mecarbam (II-1-60), methamidophos (II-1-61), methidathion (II-1-62), mevinphos (II-1-63), monocrotophos (II-1-64), naled (II-1-65), omethoate (II-1-66), oxydemeton-methyl (II-1-67), parathion (II-1-68), parathion-methyl (II-1-69), phenthoate (II-1-70), phorate (II-1-71), phosalone (II-1-72), phosmet (II-1-73), phosphamidon (II-1-74), phoxim (II-1-75), pirimiphos-methyl (II-1-76), profenofos (II-1-77), propetamphos (II-1-78), prothiofos (II-1-79), pyraclofos (II-1-80), pyridaphenthion (II-1-81), quinalphos (II-1-82), sulphotepp (II-1-83), tebupirimfos (II-1-84), temephos (II-1-85), terbufos (II-1-86), tetrachlorvinphos (II-1-87), thiometon (II-1-88), triazophos (II-1-89), trichlorfon (II-1-90), vamidothion (II-1-91)

(2) GABA-controlled chloride channel antagonists, e.g., cyclodiene organochloride type, such as chlordane (II-2-1), endosulfan (II-2-2); and phenylpyrazole type (fiprole type) such as ethiprole (II-2-3), fipronil (II-2-4)

(3) Sodium channel modulator/voltage-dependent sodium channel blocker, e.g., pyrethroids type, such as acrinathrin (II-3-1), allethrin (II-3-2), d-cis-trans allethrin (II-3-3), d-trans allethrin (II-3-4), bifenthrin (II-3-5), bioallethrin (II-3-6), bioallethrin S-cyclopentyl isomer (II-3-7), bioresmethrin (II-3-8), cycloprothorin (II-3-9), cyfluthrin (II-3-10), beta-cyfluthrin (II-3-11), cyhalothrin (II-3-12), lambda-cyhalothrin (II-3-13), gamma-cyhalothrin (II-3-14), cypermethrin (II-3-15), alpha-cypermethrin (II-3-16), beta-cypermethrin (II-3-17), theta-cypermethrin (II-3-18), zeta-cypermethrin (II-3-19), cyphenothrin [(1R)-trans isomer] (II-3-20), deltamethrin (II-3-21), empenthrin [(EZ)-(1R) isomer] (II-3-22), esfenvalerate (II-3-23), ethofenprox (II-3-24), fenpropathrin (II-3-25), fenvalerate (II-3-26), flucythrinate (II-3-27), flumethrin (II-3-28), tau-fluvalinate (II-3-29), halfenprox (II-3-30), imiprothrin (II-3-31), kadethrin (II-3-32), permethrin (II-3-33), phenothrin [(1R)trans-isomer] (II-3-34), prallethrin (II-3-35), pyrethrin (II-3-36), resmethrin (II-3-37), silafluofen (II-3-38), tefluthrin (II-3-39), tetramethrin (II-3-40), tetramethrin [(1R) isomer] (II-3-41), tralomethrin (II-3-42), transfluthrin (II-3-43); and DDT (II-3-44); and methoxychlor (II-3-45)

(4) Nicotinic acetylcholine receptor (nAChR) antagonists, e.g., neonicotinoid type, such as acetamiprid (II-4-1), clothianidin (II-4-2), dinotefuran (II-4-3), imidacloprid (II-4-4), nitenpyram (II-4-5), thiacloprid (II-4-6), thiamethoxiam (II-4-7); and nicotine (II-4-8)

(5) Nicotinic acetylcholine receptor (nAChR) allosteric activators, e.g., spinosyn type, such as spinetoram (II-5-1), spinosad (II-5-2)

(6) Chloride channel activators, e.g., avermectin type/milbemycin type, such as avamectin (II-6-1), emamectin benzoate (II-6-2), lepimectin (II-6-3), milbemectin (II-6-4)

(7) Juvenile hormone analogues, e.g., juvenile hormone analogue type, such as hydroprene (II-7-1), kinoprene (II-7-2), methoprene (II-7-3); and phenoxycarb (II-7-4); and pyriproxyfen (II-7-5)

(8) Other unspecified (multi-moiety) inhibitors, e.g., alkyl halides, such as methyl bromide (II-8-1), other alkyl halides; and chloropicrin (II-8-2), sulfuryl fluoride (II-8-3); and borax (II-8-4); and potassium antimony tartrate (II-8-5)

(9) Selective antifeedants, e.g., pymetrozine (II-9-1); and flonicamid (II-9-2)

(10) Mite growth inhibitors, e.g., clofentezine (II-10-1), hexythiazox (II-10-2), diflovidazin (II-10-3); and etoxazole (II-10-4)

(11) Destructive microorganisms of insect's digestive tract membrane, e.g., *Bacillus thuringiensis* subsp. *israelensis* (II-11-1), *Bacillus sphaericus* (II-11-2), *Bacillus thuringiensis* subsp. *aizawai* (II-11-3), *Bacillus thuringiensis* subsp. *kurstaki* (II-11-4), *Bacillus thuringiensis* subsp. *tenebrionis* (II-11-5), BT crop protein: Cry1Ab, Cry1Ac, Cry1Fa, Cry2Ab, mCry3Ab, Cry3Ab, Cry3Bb, Cry34/35Ab1 (II-11-6)

(12) Mitochondrial ATP synthase inhibitors, e.g., diafenthiuron (II-12-1); and organotin miticides, e.g., azocyclotin (II-12-2), cyhexatin (II-12-3), fenbutatin oxide (II-12-4); and propargite (II-12-5); and tetradifon (II-12-6)

(13) Oxidative phosphorylation uncouplers activated by blocking proton concentration gradient, e.g., chlorfenapyr (II-13-1), DNOC (II-13-2), sulfuramid (II-13-3)

(14) Nicotinic acetylcholine receptor (nAChR) channel inhibitors, e.g., bensultap (II-14-1), cartap hydrochloride (II-14-2), thiocyclam (II-14-3), thiosultap-sodium (II-14-4)

(15) Chitin biosynthesis inhibitors, Type 0, e.g., bistrifluoron (II-15-1), chlorfluazuron (II-15-2), diflubenzuron (II-15-3), flucycloxuron (II-15-4), flufenoxuron (II-15-5), hexaflumuron (II-15-6), lufenuron (II-15-7), novaluron (II-15-8), noviflumuron (II-15-9), teflubenzuron (II-15-10), triflumuron (II-15-11)

(16) Chitin biosynthesis inhibitors, Type 1, e.g., buprofenzin (II-16-1)

(17) Ecdysis disruptors, e.g., cyromazine (II-17-1)

(18) Ecdysone receptor antagonists, e.g., chromafenozide (II-18-1), halofenozide (II-18-2), methoxyfenozide (II-18-3), tebufenozide (II-18-4)

(19) Octopamine receptor antagonists, e.g., amitraz (II-19-1)

(20) Mitochondrial complex III electron transport inhibitors, e.g., hydramethylnon (II-20-1); and acequinocyl (II-20-2); and fluacrypyrim, (II-20-3)

(21) Mitochondrial complex I electron transport inhibitors, e.g.,

METI miticides, such as fenazaquin (II-21-1), fenpyroximate (II-21-2), pyrimidifen (II-21-3), pyridaben (II-21-4), tebufenpyrad (II-21-5), tolefenpyrad (II-21-6); and rotenone (derris) (II-21-7)

(22) Voltage-dependent sodium channel blockers, e.g., indoxacarb (II-22-1); and metaflumizone (II-22-2)

(23) Acetyl-CoA carboxylase, e.g., tetronic acid, tetramine acid derivatives, such as spirodiclofen (II-23-1), spiromesifen (II-23-2), spirotetramat (II-23-3)

(24) Mitochondrial complex IV electron transport inhibitors, e.g., phosphine type, such as aluminium phosphide (II-24-1), calcium phosphide (II-24-2), phosphine (II-24-3), zinc phosphide (II-24-4); and cyanide (II-24-5)

(25) Mitochondrial complex II electron transport inhibitors, e.g., cyenopyrafen (II-25-1)

(28) Ryanodine receptor effectors, e.g., diamide type, such as chlorantraniliprole (II-28-1), fulvenediamide (II-28-2)

(29) Other active substances with unknown or unidentified action mechanism, e.g., amidoflumet (II-29-1), azadirachtin (II-29-2), benclothiaz (II-29-3), benzoximate (II-29-4), bifenazate (II-29-5), bromopropylate (II-29-6), chinomethionat (II-29-7), cryolite (II-29-8), cyantraniliprole (cyazypyr) (II -29-9), cyflumetofen (II-29-10), dicofol (II-29-11), diflovidazin (II-29-12), fluensulfone (II-29-13), flufenerim (II-29-14), flufiprole (II-29-15), fluopyram (II-29-16), fufenozide (II-29-17), imidaclothiz (II-29-18), iprodione (II-29-19), meperfluthrin (II-29-20), pyridalyl (II-29-21), pyrifluquinazon (II-29-22), tetramethylfluthrin (II-29-23), iodomethane (II-29-24); other products derived from *Bacillus firmus* (including those other than bacterial strain CNCM I-1582 such as, VoTivo™ and BioNem) (II-29-25), and one of the following known active compounds:

3-bromo-N-{2-bromo-4-chloro-6-[(1-cyclopropylethyl)carbamoyl]phenyl}-1-(3-chloropyridin-2-yl)-1H -pyrazole-5-carboxamide (II-29-26) (disclosed in WO2005/077934), 4-{[(6-bromopyridin-3-yl)methyl](2-fluorethyl) amino}furan-2(5H)-one (II-29-27) (disclosed in WO2007/115644), 4-{[(6-fluoropyridin-3-yl)methyl](2,2-difluoroethyl) amino}furan-2(5H)-one (II-29-28) (disclosed in WO2007/115644), 4-{[(2-chloro-1,3-thiazol-5-yl)methyl](2-fluoroethyl) amino}furan-2(5H)-one (II-29-29) (disclosed in WO2007/115644), 4-{[(6-chloropyridin-3-yl)methyl](2-fluorethyl) amino}furan-2(5H)-one (II-29-30) (disclosed in WO2007/115644), flupyradifurone (II-29-31), 4-{[(6-chloro-5-fluoropyridin-3-yl)methyl](methyl) amino}furan-2(5H)-one (II-29-32) (disclosed in WO2007/115643), 4-{[(5,6-dichloropyridin-3-yl)methyl](2-fluorethyl) amino}furan-2(5H)-one (II-29-33) (disclosed in WO2007/115646), 4-{[(6-chloro-5-fluoropyridin-3-yl)methyl](cyclopropyl) amino}furan-2(5H)-one (II-29-34) (disclosed in WO2007/115643), 4-{[(6-chloropyridin-3-yl)methyl](cyclopropyl) amino}furan-2(5H)-one (II-29-35) (disclosed in EP-A -0539588), 4-{[(6-chloropyridin-3-yl)methyl](methyl)amino}furan-2 (5H)-one (II-29-36) (disclosed in EP-A -0539588), {1-(6-chloropyridin-3-yl)ethyl](methyl)oxide-λ4-sulfanylidene}cyanamide (II-29-37) (disclosed in WO2007/149134) and diastereomer thereof, {[(1R)-1-(6-chloropyridin-3-yl)ethyl](methyl)oxide-λ4-sulfanylidene}cyanamide (A) (II-29-38) (disclosed in WO2007/149134), {[(1S)-1-(6-chloropyridin-3-yl)ethyl](methyl)oxide-λ4-sulfanylidene}cyanamide (B) (II-29-39) (disclosed in WO2007/149134), sulfoxaflor (II-29-40) and diastereomer thereof,

[(R)-methyl(oxide){(1R)-1-[6-(trifluoromethyl)pyridin-3-yl]ethyl}-λ4-sulfanylidene]cyanamide (A1) (II-29-41),

[(S)-methyl(oxide){(1S)-1-[6-(trifluoromethyl)pyridin-3-yl]ethyl}-λ4-sulfanylidene]cyanamide (A2) (II-29-42) as diastereomer A group (disclosed in WO2010/074747, WO2010/074751),

[(R)-methyl(oxide){(1S)-1-[6-(trifluoromethyl)pyridin-3-yl]ethyl}-λ4-sulfanylidene]cyanamide (B1) (II-29-43),

[(S)-methyl(oxide){(1R)-1-[6-(trifluoromethyl)pyridin-3-yl]ethyl}-λ4-sulfanylidene]cyanamide (B-2) (II-29-44) as diastereomer B group (disclosed in WO2010/074747, WO2010/074751), 11-(4-chloro-2,6-dimethylphenyl)-12-hydroxy-1,4-dioxa-9-azadispiro[4.2.4.2]tetradec-11-en-10-one (II -29-45) (disclosed in WO2006/089633), 3-(4'-fluoro-2,4-dimethylbiphenyl-3-yl)-4-hydroxy-8-oxa-1-azaspiro[4,5]dec-3-en-2-one (II-29-46) (disclosed in WO2008/067911), 1-{2-fluoro-4-methyl-5-[(2,2,2-trifluoroethyl)sulfinyl]phenyl}-3-(trifluoromethyl)-1H-1,2,4-triazole-5-amine (II-29-47) (disclosed in WO2006/043635),

[(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methylcyclopropanecarboxylate (II-29-48) (disclosed in WO2008/066153), 2-cyano-3-(difluoromethoxy)-N,N'-dimethylbenzenesulfonamide (II-29-49) (disclosed in WO2006/056433), 2-cyano-3-(difluoromethoxy)-N-methylbenzenesulfonamide (II-29-50) (disclosed in WO2006/100288), 2-cyano-3-(difluoromethoxy)-N-ethylbenzenesulfonamide (II-29-51) (disclosed in WO2005/035486), 4-(difluoromethoxy)-N-ethyl-N-methyl-1,2-benzothiazole-3-amine-1,1-dioxide (II-29-52) (disclosed in WO2007/057407), N-[1-(2,3-dimethylphenyl)-2-(3,5-dimethylphenyl)ethyl]-4,5-dihydro-1,3-thiazole-2-amine (II-29-53) (disclosed in WO2008/104503), {1'-[(2E)-3-(4-chlorophenyl)prop-2-en-1-yl]-5-fluorospiro[indole-3,4'-piperidine]-1(2H)-yl}(2-chloropyridin-4-yl)methanone (II-29-54) (disclosed in WO2003/106457), 3-(2,5-dimethylphenyl)-4-hydroxy-8-methoxy-1,8-diazaspiro[4,5]dec-3-en-2-one (II-29-55) (disclosed in WO2009/049851), 3-(2,5-dimethylphenyl)-8-methoxy-2-oxo-1,8-diazaspiro[4,5]dec-3-en-4-yl-ethylcarbonate (II-29-56) (disclosed in WO2009/049851), 4-(but-2-yn-1-iloxy)-6-(3,5-dimethylpiperidin-1-yl)-5-fluoropyrimidine (II-29-57) (disclosed in WO2004/099160), (2,2,3,3,4,4,5,5-octafluoropentyl)(3,3,3-trifluoropropyl)malononitrile (II-29-58) (disclosed in WO2005/063094), (2,2,3,3,4,4,5,5-octafluoropentyl)(3,3,4,4,4-pentafluorobutyl)malononitrile (II-29-59) (disclosed in WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (II-29-60) (disclosed in WO2007/040280), frumethoxy (II-29-61), PF1364 (CAS-Reg. No. 1204776-60-2) (II-29-62) (disclosed in JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (II-29-63) (disclosed in WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (II-29-64) (disclosed in WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]benzamide (II-29-65) (disclosed in WO2005/085216), 4-{[(6-chloropyridin-3-yl)methyl](cyclopropyl)amino}-1,3-oxazol-2(5H)-one (II-29-66), 4-{[(6-chloropyridin-3-yl)methyl](2,2-difluoroethyl)amino}-1,3-oxazol-2(5H)-one (II-29-67), 4-{[(6-chloropyridin-3-yl)methyl](ethyl)amino}-1,3-oxazol-2(5H)-one (II-29-68), 4-{[(6-chloropyridin-3-yl)methyl](methyl)amino}-1,3-oxazol-2(5H)-one (II-29-69) (disclosed in WO2010/005692), NNI-0711 (II-29-70) (disclosed in WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (II-29-71) (disclosed in WO2002/096882), methyl-2-[2-({[3-bromo-1-(3-chloropyridin-2-yl)-1H-pyrazol-5-yl]carbonyl}amino)-5-chloro-3-methylbenzoyl]-2-methylhydrazinecarboxylate (II-29-72) (disclosed in WO2005/085216), methyl-2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (II-29-73) (disclosed in WO2005/085216), methyl-2-[2-({[3-bromo-1-(3-chloropyridin-2-yl)-1H-pyrazol-5-yl]carbonyl}amino)-5-cyano-3-methylbenzoyl]-2-methylhydrazinecarboxylate (II-29-74) (disclosed in WO2005/085216), methyl-2-[3,5-dibromo-2-({[3-bromo-1-(3-chloropyridin-2-yl)-1H-pyrazol-5-yl]carbonyl}amino)benzoyl]-1,2-diethylhydrazinecarboxylate (II-29-75) (disclosed in WO2005/085216), methyl-2-[3,5-dibromo-2-({[3-bromo-1-(3-chloropyridin-2-yl)-1H-pyrazol-5-yl]carbonyl}amino)benzoyl]-1,2-ethylhydrazinecarboxylate (II-29-76) (disclosed in WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (II-29-77) (disclosed in WO2007/101369), 2-{6-[2-(5-fluoropyridin-3-yl)-1,3-thiazol-5-yl]pyridin-2-yl}pyrimidine (II-29-78) (disclosed in WO2010/006713), 2-{6-[2-pyridin-3-yl-1,3-thiazol-5-yl]pyridin-2-yl}pyrimidine (II-29-79) (disclosed in WO2010/006713), 1-(3-chloropyridin-2-yl)-N-[4-cyano-2-methyl-6-(methylcarbamoyl)phenyl]-3-{(5-(trifluoromethyl)-1H -tetrazol-1-yl]methyl}-1H-pyrazole-5-carboxamide (II-29-80) (disclosed in WO2010/069502), 1-(3-chloropyridin-2-yl)-N-[4-cyano-2-methyl-6-(methylcarbamoyl)phenyl]-3-{(5-(trifluoromethyl)-2H -tetrazol-2-yl]methyl}-1H-pyrazol-5-carboxamide (II-29-81) (disclosed in WO2010/069502), N-[2-(tert-butylcarbamoyl)-4-cyano-6-methylphenyl]-1-(3-chloropyridin-2-yl)-3-{[5-(trifluoromethyl) -1H-tetrazol-1-yl]methyl}-1H-pyrazol-5-carboxamide (II-29-82) (disclosed in WO2010/069502), N-[2-(tert-butylcarbamoyl)-4-cyano-6-methylphenyl]-1-(3-chloropyridin-2-yl)-3-{[5-(trifluoromethyl) -2H-tetrazol-2-yl]methyl}-1H-pyrazol-5-carboxamide (II-29-83) (disclosed in WO2010/069502), (1E)-N-[(6-chloropyridin-3-yl)methyl]-N'-cyano-N-(2,2'-difluoroethyl)ethanimidamide (II-29-84) (disclosed in WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (II-29-85) (disclosed in CN102057925), methyl-2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (II-29-86) (disclosed in WO2011/049233)

In the pesticide preparation of the present invention, one compound (agent) may be used or a plurality of compounds may be used in combination as the pesticide active ingredients.

The content of the pesticide active ingredient is not particularly limited, but is preferably in the range of 0.01 to 50 mass %, more preferably 0.1 to 30 mass %, particularly preferably 1 to 10 mass %, on the basis of the total pesticide preparation, in view of the solubility of the pesticide active ingredient in the heat-meltable material and/or thermoplastic material in a heat-melted state.

Selective herbicidal effects between cultivated plants and weeds can be attained by the pesticide preparation according to the embodiments of the present invention. In the present specification, the weed in a broad sense means any plant that grows in undesirable places. For example, the pesticide preparation can be used for the following weeds and cultivated plants.

Genus of dicotyledonous weeds: mustard (*Sinapis*), shepherd's purse (*Capsella*), Virginia pepperweed (*Leipidium*), galium kinuta (*Galium*), chickweed (*Stellaria*), fat hen/wormseed (*Chenopodium*), velvedere (*Kochia*), nettle (*Urtica*), Aleutian Ragwort/common groundsel/ragwort (*Senecio*), pigweed/Joseph's coat (*Amaranthus*), common purslane/moss-rose purslane (*Portulaca*), common cocklebur (*Xanthium*), morning glory (*Ipomoea*), fleece flower (*Polygonum*), ragweed (*Ambrosia*), Japanese thistle/fuji thistle (*Cirsium*), common sowthistle (*Sonchus*), eggplant/potato (*Solanum*), variableleaf yellowcress (*Rorippa*), white deadnettle (*Lamium*), speedwell/geminate speedwell (*Veronica*), Angel's trumpet (*Datura*), violet pansy (*Viola*), hemp-nettle (*Galeopsis*), poppy (*Papaver*), cornflower (*Centaurea*), shaggy soldier (*Galinsoga*), rotara indica (*Rotala*), prostrate false pimpernel (*Lindernia*), hemp sesbania (*Sesbania*), white clover (*Trifolium*), abutilon theophrasti (*Abutilon*), henbit deadnettle (*Lamium*), scentless chamomile (*Matricaria*), mugwort (*Artemisia*), hemp sesbania (*Sesbania*), fiddle-leaf morning glory (*Pharbitis*), etc.

Genus of dicotyledonous cultivated plants: cotton (*Gossypium*), soybean (*Glycine*), Swiss chard/sugar beet (*Beta*), carrot (*Daucus*), common bean/aoimada (*Phaseolus*), pea (*Pisum*), eggplant/potato (*Solanum*), flax (*Linum*), sweet potato/morning glory (*Ipomoea*), broad bean/vetches (*Vicia*), tobacco (*Nicotiana*), tomato (*Lycopersicon*), peanut (*Arachis*), Chinese colza/Chinese cabbage/turnip/cabbage (*Brassica*), Indian lettuce (*Lactuca*), cucumber/melon (*Cucumis*), pumpkin (*Cucurbita*), etc.

Genus of monocotyledonous weeds: Japanese barnyard millet (*Echinochlona*), green bristlegrass/foxtail millet (*Setaria*), millet (*Panicum*), crabgrass (*Digitaria*), sand Cat's-Tail/timothy (*Phleum*), bluegrass/annual bluegrass (*Poa*), sheep's fescue/toboshigara (*Festuca*), Indian goosegrass/finger millet (*Eleusine*), darnel (*Lolium*), kitsunegaya/rescuegrass (*Bromus*), common wild oat/oat (*Avera*), Asian flatsedge/papyrus/Chinese matgrass/purple nut sedge (*Cyperus*), sorghum (*Sorghum*), wheat grass (*Agropyron*), konagi (*Monochoria*), fimbry (*Fimbristylis*), arrowhead/threeleaf arrowhead (*Sagittaria*), spikerushe/water chestnut (*Eleocharis*), scirpus hotarui/scirpus yagara/futoi (*Scirpus*), dallis grasses (*Paspalum*), kamonohashi (*Ischaemum*), nukabo (*Agrostis*), orange foxtail (*Alopecurus*), bermudagrass (*Cynodon*), Asiatic dayflower (*Commelina*), Alexandergrass (*Brachiaria*), Red sprangletop (*Leptochloa*) etc.

Genus of monocotyledonous cultivated plants: rice (*Oryza*), corn/popcorn (*Zea*), wheat (*Triticum*), barley (*Hordeum*), common wild oat/oat (*Avera*), rye wheat (*Secale*), sorghum (*Sorghum*), millet (*Panicum*), sugarcane/waseobana (*Saccharum*), pineapple (*Ananas*), asparagus (*Asparagus*), Welsh onion/garlic chives (*Allium*), etc.

Selective herbicidal effects between paddy rice and paddy field weeds can be attained by the pesticide preparation according to the embodiments of the present invention. Examples of the controllable paddy field weeds include the following:

Dicotyledonous plants belonging to the following genus: *Polygonum, Rorippa, Rotala, Lindemia, Bidens, Dopatrium, Eclipta, Elatine, Gratiola, Lindemia, Ludwigia, Oenanthe, Ranunculus, Deinostema*, etc.

Monocotyledonous plants belonging to the following genus: *Echinochloa, Panicum, Poa, Cyperus, Monochoria, Fimbristylis, Sagittaria, Eleocharis, Scirpus, Alisma, Aneilema, Blyxa, Eriocaulon, Potamogeton, Brachiaria, Leptochloa, Sphenoclea*, etc.

More specifically, the pesticide preparation can be used for the following representative paddy field weeds.

Plant names Latin names
Dicotyledonous plants
Water clover *Marisilea quadrifolia*
Globe fringerush *Fimbristylis miliacea*
Gooseweed *Sphenoclea zeylanica*
Himemisohagis *Ammannia* sp.
Rotala indica *Rotala indica Koehne*
Prostrate false pimpernel *Lindemia procumbens Philcox*
Green amaranth *Amaranthus viridis*
Yellowseed false pimpernel *Lindemia dubia L. Penn.*
False daisy *Eclipta prostrata*
Azetogarashi *Lindernia angustifolia*
Chiyoujitade *Ludwigia prostrata Roxburgh*
Tades *Polygonum* sp.
Hemp sesbania *Sesbania exaltata*
Pondweed *Potamogeton distinctus A. Benn*
Whitestar *Ipomoea lacunosa*
Three-stamen waterwort *Elatine triandra Schk*
Water dropwort *Oenanthe javanica*
Monocotyledonous plants
Barnyardgrass *Echinochloa oryzicola Vasing*
Wild millet *Echinochlor colonum*
Cockspur grass *E. crus-galli*
Saramolla *Ischaemum rugosum*
Millets *Panicum* sp.
Indian goosegrass *Eleusine indica*
Crabgrass *Digitaria* sp.
Knotgrass *Paspalum distichum*
Rice flat sedge *Cyperus iria*
Purple nut sedge *C. rotundus*
Needle spikerush *Eleocharis acicularis L.*
Water chestnut *Eleochris kuroguwai Ohwi*
Coco-grass *Cyperus difformis L.*
Water nutgrass *Cyperus serotinus Rottboel*
Ricefield Bulrush *Scirpus mucronatus*
Seaside Bulrush *S. planiculmis*
Scirpus hotarui *Scirpus juncoides Roxburgh*
Konagi *Monochoria vaginalis Presl*

Pygmy arrowhead *Sagittaria pygmaea Miq*
Heraomodaka *Alisma canaliculatum A. Br. et Bouche*
Mad-dog weed *A. plantago-aquatica*
Arrowhead *Sagittaria trifolia*
Mizuaoi *Monochoria korsakowii*
Alexandergrass *Brachiaria plantaginea*
Red sprangletop *Leptochloa chinensis*

The pesticide preparation of the present invention is not limited to use for these varieties of weeds but is applicable to other varieties of weeds as well.

An insecticide can be used as the pesticide active ingredient contained in the pesticide preparation of the present invention. The pesticide preparation according to one embodiment of the present invention exhibits precise control effects on harmful insects without causing chemical damages to cultivated plants. Further, the pesticide preparation of the present invention can be used to control a wide variety of pests such as detrimental sap-sucking insects, chewing insects and other plant-parasitic pests, and hence applicable to control and eradicate them.

Examples of such pests include the following pests.
Insecta includes;
coleoptera pests such as azuki bean beetle (*Callosobruchus Chinensis*), rice weevil (*Sitophilus zeamais*), flour beetle (*Tribolium castaneum*), 28-spotted potato ladybird (*Epilachna vigintioctomaculata*), barley wireworm (*Agriotes ogurae fuscicollis*), soybean beetle (*Anomala rufocuprea*), Colorado potato beetle (*Leptinotarsa decemlineata*), corn root worms (*Diabrotica* spp.), sawyer beetle (*Monochamus alternatus endai*), rice water weevil (*Lissorhoptrus oryzophilus*), powder-post beetle (*Lyctus brunneus*);
arguloida pests such as gypsy moth (*Lymantria dispar*), lackey moth (*Malacosoma neustria*), cabbage white (*Pieris rapae crucivora*), oriental leafworm moth (*Spodoptera litura*), cabbage moth (*Mamestra brassicae*), rice stem borer (*Chilo suppressalis*), European corn borer (*Ostrinia nubilalis*), tropical warehouse moth (*Cadra cautella*), smaller tea tortrix (*Adoxophyes honmai*), codling moth (*Cydia pomonella*), turnip moth (*Agrotis segetum*), greater wax moth (*Galleria mellonella*), diamondback moth (*Plutella xylostella*), tobacco budworm (*Heliothis virescens*), citrus leafminer (*Phyllocnistis citrella*);
hemiptera pests such as green rice leafhopper (*Nephotettix cincticeps*), brown planthopper (*Nilaparvata lugens*), comstock mealybug (*Pseudococcus comstocki*), arrowhead scale (*Unaspis yanonensis*), green peach aphid (*Myzus persicas*), green apple aphid (*Aphis pomi*), cotton aphid (*Aphis gossypii*), mustard aphid (*Lipaphis erysimi*), pear lace bug (*Stephanitis nashi*), stink bugs (*Nezara* spp.), greenhouse whitefly (*Trialeurodes vaporariorum*), psyllids (*Psylla* spp.);
thysanoptera pests such as melon thrip (*Thrips palmi*), western flower thrip (*Franklinella occidentalis*);
orthoptera pests such as African mole cricket (*Gryllotalpa africana*), migratory locust (*Locusta migratoria*);
blattodea pests such as german cockroach (*Blatella germanica*), American cockroach (*Periplaneta americana*), reticulitermes (*Reticulitermes speratus*), coptotermes (*Coptotermes formosanus*);
diptera pests such as common housefly (*Musca domestica*), yellow fever mosquito (*Aedes aegypti*), bean seed fly (*Delia platura*), northern house mosquito (*Culex pipiens pallens*), Chinese anopheles (*Anopheles sinensis*), kogataakaieka (*Culex tritaeniorhynchus*), burgess (*Liriomyza trifolii*), and the like.

Further, examples of mites include carmine spider mite (*Tetranychus cinnabarinus*), two-spotted spider mite (*Tetranychus urticae*), pink citrus rust mite (*Panonychus citri*), mandarin orange rust mite (*Aculops pelekassi*), housedust mites (*Tarsonemus* spp.), and the like.

Furthermore, examples of nematoda include such as sweet potato root-knot nematode (*Meloidogyne incognita*), pine wood nematode (*Bursaphelenchus xylophilus*), strawberry crimp disease nematode (*Aphelenchoides besseyi*), soybean cyst nematode (*Heterodera glycines*), root lesion nematode (*Pratylenchus* spp.), and the like.

A disinfectant can be used as the pesticide active ingredient contained in the pesticide preparation of the present invention. The pesticide preparation can commonly be used as a disinfectant (fungicide) for a wide range of plants attacked by Plasmodiophoromycetes, Oomycetes, Zygomycetes, Ascomycetes, Basidiomycetes and Deuteromycetes. The pesticide preparation shows particularly good controlling effects on plant pathogens such as *Gibberella fujikuroi*, *Pyriculaia oryzae*, *Cochliobolus miyabeanus*, and the like.

In the present invention, the amine containing a group having a hydrophobic moiety on a nitrogen atom is not particularly limited, but, for example, preferable is the amine, owing to the capability of forming a particularly stable association with many pesticide active ingredients, represented by the following general formula:

(I)

wherein $R^1$ is a group having 3 to 20 carbon atoms, preferably 3 to 10 carbon atoms, as the group containing a hydrophobic moiety, $R^2$ and $R^3$ are independently a hydrogen atom or a saturated or unsaturated, substituted or unsubstituted hydrocarbon group.

The group having 3 to 10 carbon atoms as the group having a hydrophobic moiety preferably has an aromatic ring as the hydrophobic moiety. The amine having an aromatic ring forms a particularly stable association with a pesticide active ingredient having an aromatic ring. The aromatic ring may contain a hetero atom or may further be substituted with a suitable substituent such as a halogen atom, or the like. Specific examples of the aromatic ring include benzene ring, naphthalene ring, pyridine ring, pyrrole ring, quinoline ring, toluidine ring, indole ring, imidazole ring, and pyrazine ring. Examples of the saturated or unsaturated hydrocarbon group include alkyl group (cycloalkyl group, linear chain or branched chain alkyl group), alkenyl group, alkynyl group, and aryl group. Examples of the substituent include halogen atoms such as chloro and bromo, phospho group, sulfo group, aldehyde group, alkoxy carbonyl group, hydroxy group, oxydialkyl group, amino group, and =O. Specific examples of the above amine include aniline, diphenylamine, N,N-dimethylaniline, N-methylaniline, N,N-diethylaniline, N-ethylaniline, dibenzylamine, and acetanilide, preferably N,N-diethylaniline and diphenylamine, and more preferably diphenylamine. The amine may be used individually or two or more may be used in combination in any ratio. The content of the amine containing a group having a hydrophobic moiety on a nitrogen atom is preferably 0.01 to 10 mass %, more preferably 0.3 to 5 mass %, on the basis of the total pesticide preparation. Further, the amine is preferably used in a range of 0.01 to 10 mol, particularly 1 to 3 mol, per mol of the pesticide active ingredient.

The heat-meltable material and thermoplastic material usable in the present invention are not particularly limited, but those which are solid at room temperature (25° C.) and have a melting point or a softening point within a range of 50 to 160° C., particularly hydrophobic organic materials are preferable. The hydrophobic organic material preferably has a solubility of 50 ppmw or less in water at room temperature. To maintain the sustained release properties, the solubility of the hydrophobic organic material in water is preferably 20 ppmw or less, more preferably 10 ppmw or less, particularly preferably 5 ppmw or less. Specific examples of the heat-meltable material and thermoplastic material include plant waxes such as candelilla wax, carnauba wax, sugarcane wax, and rice wax, mineral waxes such as montanic acid wax, ozokerite, and ceresin, petroleum waxes such as paraffin wax, microcrystalline wax and petrolatum, synthetic hydrocarbons such as Fischer-Tropsch wax, modified waxes such as montanic acid wax derivatives, paraffin wax derivatives, and microcrystalline wax derivatives, fatty acids such as stearic acid and behenic acid, hydrogenated castor oil, hydrogenated waxes such as hydrogenated castor oil derivatives, higher alcohols such as stearyl alcohol, fatty acid esters of fatty acids such as stearylstearate and higher alcohols, fatty acids such as 12-hydroxystearic acid, octadecanamide, and chlorinated hydrocarbon, non-aromatic materials such as acid amide, ester, and ketone, polycyclic aromatic hydrocarbons such as biphenyl (melting point 68.9° C.), triphenylmethane (melting point 93.4° C.), phenanthrene (melting point 100° C.), fluorene (melting point 116° C.), acenaphthene (melting point 92° C.), and fluoranthene (melting point 109° C.), and aromatic thermoplastic materials such as 2-chloronaphthalene (melting point 59.5° C.), triphenylphosphine (melting point 80° C.), diphenyl-phthalate (melting point 75° C.), dicyclohexyl phthalate (melting point 61° C.), triphenylamine (melting point 126° C.), p-(a-cumyl)phenol (melting point 72° C.), diphenylsulfone (melting point 128° C.), naphthol (melting point 96° C.), bisphenol A (melting point 152° C.), phenylphenol (melting point 56° C.), benzyl (melting point 95° C.), thermoplastics (cumarone plastics having a softening point of 70 to 90° C., etc.), and asphaltene. These materials may be used individually or two or more may be used in combination in any ratio. The mixing ratio of the heat-meltable material and/or thermoplastic material is preferably 1 to 60 mass %, more preferably 20 to 40 mass %, on the basis of the total mass of the pesticide preparation of the present invention.

Examples of the carrier usable in the present invention include oil adsorbent granular carriers and/or oil absorbent granular carriers including mineral matters such as calcium montmorillonite, attapulgite, pumice, perlite, diatomaceous earth, vermiculite, talc, and clay. A binder used for the granulation can also be used, and specific examples of the binder include vegetable matters such as pulp effluent. Examples of the commercial products used as the carrier include AGSORB (attapulgite produced by Oil-Dri Corporation), CELATOM (diatomaceous earth produced by EaglePicher Corporation), ISHIKAWALITE (pumice produced by IshikawaLite Industry CO., LTD.), APLS (diatomaceous earth granulated product produced by ISOLITE Insulating Products Co., Ltd.), ISOLITE (diatomaceous earth produced by ISOLITE Insulating Products Co., Ltd.), BIODAC (pulp effluent granulated product produced by Edward Lowe Industries, Inc.), and perlite (perlite produced by EaglePicher Corporation. The particle diameter of the carrier used in the present invention is preferably 250 μm or more, and the maximum particle diameter is preferably 3,000 μm or less. The content of the carrier is usually 30 to 99.9 mass %, particularly 60 to 99.9 mass %, preferably 65 to 99 mass %, on the basis of the total mass of the pesticide preparation of the present invention.

The pesticide preparation according to the present invention can contain, in addition to the above components, publicly known additives. Specific examples include antioxidants (BHT, BHA, etc.), epoxidized soybean oils (Newkalgen NK-800, etc.), and thermoplastic synthetic resins (Hariester NL, cumarone G-90, etc.).

The process for producing the pesticide preparation according to the present invention is not particularly limited, and, for example, the preparation can be produced by mixing under heating (preferably at a temperature equal to or higher than a melting point or a softening point of a heat-meltable material or thermoplastic material) a pesticide active ingredient, an amine being capable of forming an associated state with the pesticide active ingredient and containing a group having a hydrophobic moiety on a nitrogen atom, a heat-meltable material and/or thermoplastic material, and an optionally added carrier. The pesticide preparation according to the present invention is preferably a granular product, and publicly known methods such as the extrusion granulation method can be applied if necessary to the granulation.

The pesticide preparation of the present invention can be used, for example, by spraying over a paddy field immediately after paddy rice transplantation, but can also be applied during soil incorporation, planting hole treatment, plant foot treatment, etc.

Next, the production and application of the compound of the present invention are further specifically described in reference to the Examples below, but the present invention is not limited thereto. In the production examples below, part means part by mass.

EXAMPLE 1

SN12

Three parts of tefuryltrione, 1.15 parts of diphenylamine and 29 parts of biphenyl were put in an Erlenmeyer flask and heated at 90° C. in a water bath to obtain a molten mixture. 66.7 parts of ISOLITE (diatomaceous earth produced by ISOLITE Insulating Products Co., Ltd., oil absorption capacity is about 80% of self weight) having been heated to 90° C. in advance was added to the molten mixture, well mixed and further cooled down to room temperature to obtain a granular preparation.

EXAMPLE 2

SN13

A granular preparation was obtained by the same operation as described in Example 1 except that triphenylmethane was used in place of biphenyl in Example 1.

EXAMPLE 3

SN27

A granular preparation was obtained by the same operation as described in Example 1 except that the amount of biphenyl added in Example 1 was reduced to 22.4 parts and 6.67 parts of paraffin wax (by NIPPON SEIRO CO., LTD., melting point 75° C.) was used instead.

EXAMPLE 4

SN32

A granular preparation was obtained by the same operation as described in Example 3 except that N,N-dimethylaniline was used in place of diphenylamine in Example 3.

EXAMPLE 5

SN33

A granular preparation was obtained by the same operation as described in Example 4 except that N-methylaniline was used in place of diphenylamine in Example 4.

COMPARATIVE EXAMPLE 1

SN10

A granular preparation was obtained by the same operation as described in Example 1 except that Hisol SAS-296, an aromatic high-boiling point solvent (mixture of 1-phenyl-1-xylylethane and 1-phenyl-1-ethylphenylethane, trade name of a product produced by Japan Oil Co., Ltd.) was used in place of biphenyl in Example 1.

COMPARATIVE EXAMPLE 2

SN23

A granular preparation was obtained by the same operation as described in Example 1 except that biphenyl was used in place of diphenylamine in Example 1.

COMPARATIVE EXAMPLE 3

SN34

The same operation as described in Example 1 was conducted with an exception of using diethylamine in place of diphenylamine in Example 3, but the pesticide active ingredient was crystallized and a homogeneous molten mixture could not be obtained causing the failure in producing a granular preparation.

COMPARATIVE EXAMPLE 4

SN36

The same operation as described in Example 3 was conducted with an exception of using biphenyl in place of diphenylamine in Example 3, but the solubility of the pesticide active ingredient was insufficient and a homogeneous molten mixture could not be obtained causing the failure in producing a granular preparation.

Test to Verify the Amine Effect on the Active Ingredient Solubility in an Impregnation Solution To 31.0 g of tefuryltrione and 11.5 g of diphenylamine (equivalent mol to tefuryltrione), 10 mL of toluene was added and refluxed under heating at 90° C. for 1 hour. Toluene was distilled off from the obtained molten product to obtain a crystal mixture of tefuryltrione and diphenylamine. The melting point of the obtained compound was measured using a DSC (Differential Scanning calorimetry) and compared with those of the starting materials (Table 1).

TABLE 1

| Compound tested | Melting point (° C.) |
| --- | --- |
| Tefuryltrione | 107 |
| Diphenylamine association with tefuryltrione | 103.9 |
| Diphenylamine | 48.1 |

It is shown that an association of the pesticide active ingredient tefuryltrione and diphenylamine is formed.

Verification Test for Lipophilicity Effected by the Association Formation of the Pesticide Active Ingredient Tefuryltrione and Diphenylamine The solubilities of the pesticide active ingredients in toluene and a toluene/isooctane mixture liquid (80/20, v/v) at room temperature were determined (Table 2).

TABLE 2

| | Solubility (g/L) | |
| --- | --- | --- |
| Compound tested | Toluene | Toluene/isooctane mixture liquid (80/20, v/v) |
| Tefuryltrione | 97.8 | 49.4 |
| Diphenylamine association with tefuryltrione | >300 | 171 |

It is suggested that the association formation improved lipophilicity of tefuryltrione.

Dissolution Test in Water

Fifty mg of each of the granular preparations obtained in the above Examples and Comparative Examples was treated in a dissolution tester (produced by Entec Co., Ltd., Hi-PACK) filled with 1,250 mL of 3-degree hard water. The ingredient concentration in 3-degree hard water was measured time-dependently by the liquid chromatography technique, and the dissolution rate was calculated (ingredient concentration in 3-degree hard water/ingredient concentration when all ingredients in each granular preparation were dissolved in 3-degree hard water×100). Table 3 shows the test results.

TABLE 3

| | Dissolution time (day(s)) | | | |
| --- | --- | --- | --- | --- |
| | 1 | 2 | 3 | 21 |
| Example 1 | 69.9 | 77.6 | 83.8 | 95.6 |
| Example 2 | 39.7 | 51.0 | 59.7 | 84.1 |
| Example 3 | 39.7 | 51.4 | 61.3 | 93.3 |
| Example 4 | 42.6 | 51.2 | 58.9 | 88.0 |
| Example 5 | 47.7 | 60.8 | 69.8 | 92.8 |
| Comparative Example 1 | 99.9 | 98.7 | 100.1 | 101.5 |
| Comparative Example 2 | 53.9 | 60.7 | 64.5 | 76.8 |
| Comparative Example 3 | Granular preparation could not be prepared. | | | |
| Comparative Example 4 | Granular preparation could not be prepared | | | |

As is evident from Table 3, according to the method of the present invention, the granular preparations of Examples 1 to 5 containing the amine being capable of forming an associated state with the pesticide active ingredient and containing a group having a hydrophobic moiety on a nitrogen atom and a thermoplastic material could provide molten mixtures and exhibited stable sustained release properties. This is attributed that the amine associates with the pesticide active ingredient to form an association with lipophilic substituents positioned around its outer periphery, resulting in enhanced lipophilicity, and the pesticide active ingredient is homogeneously dispersed and sustained in the thermoplastic material. Example 2, wherein biphenyl (water solubility 7 ppm) in Example 1 was replaced with triphenylmethane (water insoluble), could better suppress the dissolution compared with Example 1. Example 3, wherein a part of biphenyl was replaced with paraffin wax, could better suppress the initial dissolution compared with Example 1. In contrast, in Comparative Example 1, the oil substance floated quickly on the water surface and the dissolution could not be suppressed. In Comparative Example 2, the initial dissolution could be suppressed but even 21 days later, 20% or more of the ingredients were found to remain in the preparation. In Comparative Example 3, the diethylamine association did not have sufficient solubility in the mixture and a granular preparation could not be prepared.

These results reveal that the pesticide preparation of the present invention has advantages of being capable of controlling the release of the pesticide active ingredients as necessary and most of the pesticide active ingredients in the preparation are dissolved after a certain period of time has passed. These advantages lead to maintaining good biological effects over an extended period of time as well as being capable of reducing phytotoxicity on useful plants.

The invention claimed is:

1. A pesticide preparation comprising as pesticide active ingredient a herbicide for paddy field weed and a heat-meltable material and/or a thermoplastic material, which is a wax, a polycyclic aromatic hydrocarbon, or a mixture thereof the pesticide preparation further comprising an amine, wherein the amine is represented by formula (I)

(I)

wherein
$R^1$ is a group having 3 to 20 carbon atoms as the group having a hydrophobic moiety and which is selected from the group consisting of a substituted or unsubstituted phenyl group, benzyl group, pyridyl group, pyrrolyl group, quinolyl group, toluidyl group, indolyl group, imidazolyl group, and pyrazyl group, and
$R^2$ and $R^3$ are independently a hydrogen atom or a saturated or unsaturated, substituted or unsubstituted hydrocarbon group.

2. The pesticide preparation according to claim 1, wherein the amine is at least one amine selected from the group consisting of aniline, diphenylamine, N,N-dimethylaniline, N-methylaniline, N,N-diethylaniline, N-ethylaniline and dibenzylamine.

3. The pesticide preparation according to claim 1, wherein the amine is at least one amine selected from the group consisting of diphenylamine, N,N-dimethylaniline and N-methylaniline.

4. The pesticide preparation according to claim 1, wherein the pesticide active ingredient comprises at least one compound selected from the group consisting of pyrimisulfan, triafamone, tefuryltrione, ketospiradox, mesotrione, sulcotrione and tembotrione.

5. The pesticide preparation according to claim 1,
further comprising a carrier,
the carrier being at least one selected from the group consisting of calcium montmorillonite, attapulgite, pumice, perlite, diatomaceous earth, vermiculite, talc and clay.

6. A process for producing the pesticide preparation according to claim 1, the process comprising:
mixing a pesticide active ingredient, an amine of formula (I), a heat-meltable material and/or a thermoplastic material, which is a wax, polycyclic aromatic hydrocarbon or a mixture thereof, and a carrier under heating.

7. The pesticide preparation according to claim 1, wherein the amine is diphenylamine.

8. The pesticide preparation according to claim 1, wherein the amine is N,N-dimethylaniline.

9. The pesticide preparation according to claim 1, wherein the amine is N-methylaniline.

10. The pesticide preparation according to claim 1, wherein the pesticide active ingredient comprises pyrimisulfan.

11. The pesticide preparation according to claim 1, wherein the pesticide active ingredient comprises triafamone.

12. The pesticide preparation according to claim 1, wherein the pesticide active ingredient comprises tefuryltrione.

13. The pesticide preparation according to claim 1, wherein the pesticide active ingredient comprises ketospiradox.

14. The pesticide preparation according to claim 1, wherein the pesticide active ingredient comprises mesotrione.

15. The pesticide preparation according to claim 1, wherein the pesticide active ingredient comprises sulcotrione.

16. The pesticide preparation according to claim 1, wherein the pesticide active ingredient comprises tembotrione.

17. A method of killing a weed in a paddy field comprising applying the pesticide preparation according to claim 1 to said weed.

* * * * *